(12) United States Patent
Arnon et al.

(10) Patent No.: US 6,740,325 B1
(45) Date of Patent: May 25, 2004

(54) PEPTIDE-BASED VACCINE FOR INFLUENZA

(75) Inventors: Ruth Arnon, Rehovot (IL); Tamar Ben-Yedidia, Mazkeret Batya (IL); Raphael Levi, Yahud (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 09/856,920

(22) PCT Filed: Nov. 28, 1999

(86) PCT No.: PCT/IL99/00640
§ 371 (c)(1),
(2), (4) Date: Jul. 30, 2001

(87) PCT Pub. No.: WO00/32228
PCT Pub. Date: Jun. 8, 2000

(30) Foreign Application Priority Data

Nov. 30, 1998 (IL) .................................. 127331

(51) Int. Cl.[7] ............................................. A61K 39/145
(52) U.S. Cl. ................. 424/206.1; 424/204.1; 530/300; 435/320.1; 435/6
(58) Field of Search ............. 424/206.1, 204.1; 530/300; 435/6, 320.1

(56) References Cited

FOREIGN PATENT DOCUMENTS

WO    WO 93/20846    10/1993

OTHER PUBLICATIONS

Tamar Ben–Yedidia, et al. Intranasal administrationof peptide vaccine protects human/mouse radiation chimera from influenza infection. Dept. of Immunology, The Weizmann Institute Science, Rehovot, Israel.

Francine Connan, et al. A simple assay for detection of peptides promoting the assembly of HLA class I molecules. Eur. J. Immunol. 1994. 24: 777–780.

Jeff Alexander, et al. Derivation of HLA–A11/$K^b$ Transgenic Mice. The American Association of Immunologists (1977).

Tao Dong, et al. An HLA–B35–restricted epitope modified at an anchor residue results in an antagonist peptide. Eur. J. Immunol. 1996 26: 335–339.

Sutton, Julian, et al. A sequence pattern for peptides presented to cytotoxic T lymphocytes by HLA B8 revealed by analysis of epitopes and eluted peptides. European Journal of Immunology (1993).

Jonathan B. Rothbard, et al. Structural Model of HLA–DR1 Restricted T Cell Antigen Recognition. Cell. vol 52, 515–523. (Feb. 26, 1988).

Raphael Levi, et al. Synthetic recombinant influenza vaccine induces efficient long–term immunity and cross–strain protection. Vaccine vol. 14, No. 1, pp. 85–92 (1996) Elsevier Sceince Ltd.

Tamar Ben–Yedidia, et al. Efficacy of anti–influenza peptide vaccine in aged mice. Mechanisms of ageing and development, 104 (1998) 11–23.

*Primary Examiner*—Ali R. Salimi
(74) *Attorney, Agent, or Firm*—G.E. Ehrlich (1995) Ltd.

(57) ABSTRACT

A human synthetic peptide-based influenza vaccine for intranasal administration comprises a mixture of flagella containing at least four epitopes of influenza virus reactive with human cells, each expressed individually in Salmonella flagellin, said influenza virus epitopes being selected from the group consisting of: (i) one B-cell hemagglutinin (HA) epitope; (ii) one T-helper hemagglutinin (HA) or nucleoprotein (NP) epitope that can bind to many HLA molecules; and (iii) at least two cytotoxic lymphocyte (CTL) nucleoprotein (NP) or matrix protein (M) epitopes that are restricted to the most prevalent HLA molecules in different human populations.

6 Claims, 4 Drawing Sheets

Figure 3:
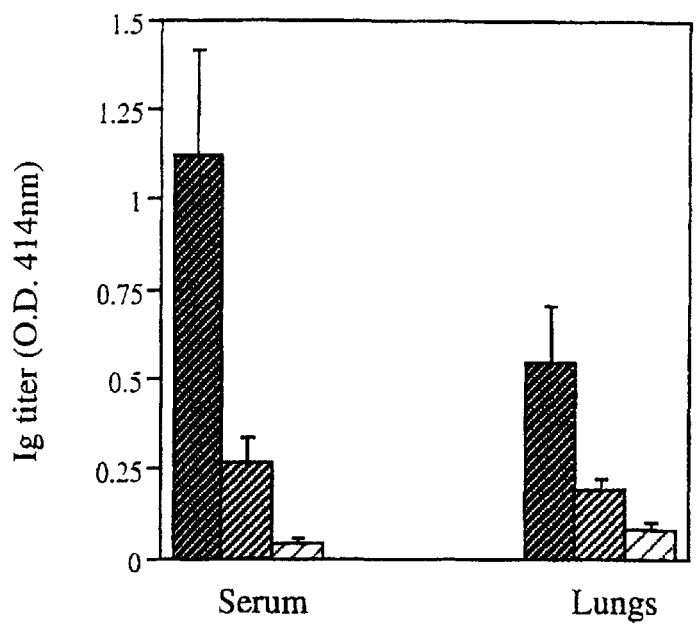

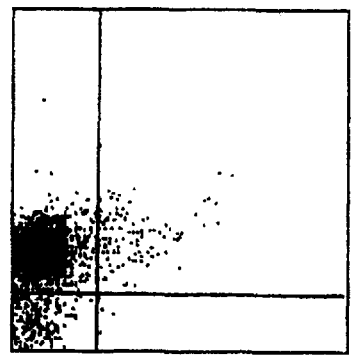
Fig. 1A  Fig. 1B
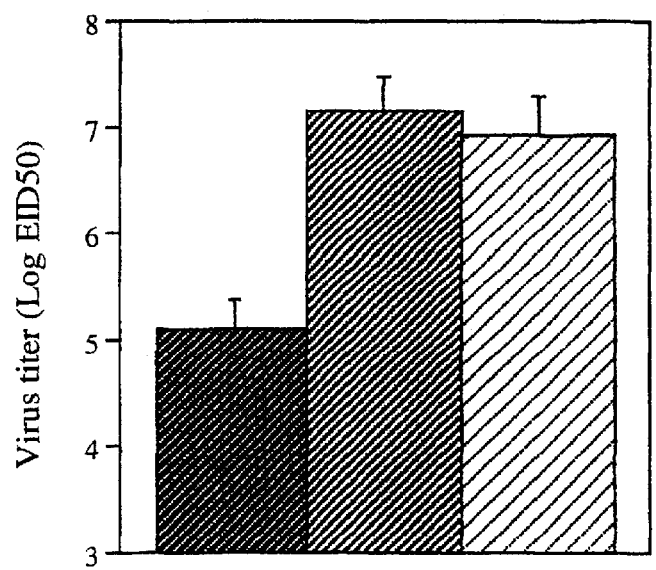
Fig. 2

Days after transplantation

Days after transplantation

PEPTIDE-BASED VACCINE FOR INFLUENZA

CROSS-REFERENCE TO RELATED APPLICATIONS

This patent application is a National Phase Concerning a Filing Under 35 U.S.C. 371, claiming the benefit of priority of PCT/IL99/00640, filed Nov. 28, 1999, which claims the benefit of priority of Israeli Patent Serial No. 127331, filed Nov. 30, 1998, all of which are incorporated herein by reference.

FIELD OF THE INVENTION

The present invention relates to influenza vaccines, and particularly to peptide-based vaccines comprising conserved epitopes of both B and T-lymphocytes recognized by the prevalent HLA's in humans.
ABBREVIATIONS: Ab: Antibodies; CTL: Cytotoxic T-lymphocytes; EID: Egg-infective dose; HA: Hemagglutinin; HAU: Hemagglutination unit; i.n.: intranasal; i.p.: intraperitoneal; NP: Nucleoprotein; PMBC: Peripheral blood mononuclear cells; TT: Tetanus toxoid.

BACKGROUND OF THE INVENTION

Influenza is a public health concern, it results in economic burden, morbidity and even mortality. Influenza infection may result in a variety of disease states, ranging from sub-clinical infection through a mild upper respiratory infection and tracheobronchitis to a severe occasionally lethal viral pneumonia. The reasons for this wide spectrum of severity are explained by the site of infection and the immune status of the host. The most important characteristic of influenza, from the immunological point of view, is the rapid, unpredictable changes of the surface glycoproteins, haemagglutinin and neuraminidase, referred to as antigenic shifts and drifts. These changes lead eventually to the emergence of new influenza strains, that enable the virus to escape the immune system and are the cause for almost annual epidemics (Laver et al., 1980 and 1980a; Webster, 1982).

Immunization towards influenza virus is limited by this marked antigenic variation of the virus and by the restriction of the infection to the respiratory mucous membranes. The influenza vaccines currently available and licensed are based either on whole inactive virus, or on viral surface glycoproteins. These influenza vaccines fail to induce complete, long-term and cross-strain immunity.

Influenza virus comprises two surface antigens: neuraminidase (NA) and hemagglutinin (HA), which undergo gradual changes (shifts and drifts), leading to the high antigenic variations in influenza. HA is a strong immunogen and is the most significant antigen in defining the serological specificity of the different virus strains. The HA molecule (75–80 kD) comprises a plurality of antigenic determinants, several of which are in regions that undergo sequence changes in different strains (strain-specific determinants) and others in regions which are common to many HA molecules (common determinants).

U.S. Pat. No. 4,474,757 describes a synthetic vaccine against a plurality of different influenza virus comprising a suitable macromolecular carrier having attached thereto a peptide being an antigenic fragment of HA which is common to a plurality of different influenza virus strains. One of the described common determinants is the HA epitope 91–108 which is conserved in all H3 influenza subtype strains.

The nucleoprotein (NP) is located in the viral core and is one of the group specific antigens which distinguishes between influenza A, B and C viruses. In contrast to the HA, the NP is one of the most conserved viral proteins, being 94% conserved in all influenza A viruses. Influenza A virus NP-specific antibody has no virus neutralizing activity, but NP is an important target for cytotoxic T lymphocytes (CTL) which are cross-reactive with all type A viruses (Townsend and Skehel, 1984). CTL recognize short synthetic peptides corresponding to linear regions of the influenza NP molecule (Townsend et al., 1985 and 1986).

PCT International Publication WO 93/20846 describes a synthetic recombinant vaccine against a plurality of different influenza virus strains comprising at least one chimeric protein comprising the amino acid sequence of flagellin and at least one amino acid sequence of an epitope of influenza virus HA or NP, or an aggregate of said chimeric protein. Following this approach, a synthetic recombinant anti-influenza vaccine based on three epitopes was found to be highly efficient in mice. This vaccine included HA 91–108, a B cell epitope from the HA which is conserved in all H3 strains and elicits anti-influenza neutralizing antibodies, together with a T-helper and CTL epitopes from the NP(NP 55–69 and NP 147–158, respectively), which induce MHC-restricted immune responses. Each of these epitopes was expressed in the flagellin of Salmonella vaccine strain. The isolated flagella were administered intranasally to mice, resulting in protection against viral infection (Levi and Arnon, 1996).

SUMMARY OF THE INVENTION

According to the present invention, influenza peptide epitopes reactive with human cells were expressed in Salmonella flagellin and tested for efficacy in a human/mouse radiation chimera in which human PBMC were functionally engrafted. Clearance of the virus after challenge and resistance to lethal infection was found only in the vaccinated mice and production of virus specific human antibodies was also higher in this group. FACS analysis showed that most human cells in the transplanted mice were CD8+ and CD4+, indicating that the protection was mediated mainly by the cellular immune response.

The present invention thus relates to a human synthetic peptide-based influenza vaccine for intranasal administration comprising a mixture of flagella containing at least four epitopes of influenza virus each expressed individually in Salmonella flagellin, said influenza virus epitopes being reactive with human cells and being selected from the group consisting of: (i) one B-cell hemagglutinin (HA) epitope; (ii) one T-helper hemagglutinin (HA) or nucleoprotein (NP) epitope that can bind to many HLA molecules; and (iii) at least two cytotoxic lymphocyte (CTL) nucleoprotein(NP) or matrix protein (M) epitopes that are restricted to the most prevalent HLA molecules in different human populations.

The preferred B-cell HA epitope is the influenza virus hemagglutinin epitope 91–108 [HA 91–108] of the sequence:

Ser-Lys-Ala-Phe-Ser-Asn-Cys-Tyr-Pro-Tyr-Asp-Val-Pro-Asp-Tyr-Ala-Ser-Leu

The preferred T-helper epitopes are the influenza virus hemagglutinin epitope 307–319 [HA 307–319] of the sequence:

Pro-Lys-Tyr-Val-Lys-Gln-Asn-Thr-Leu-Lys-Leu-Ala-Thr
and the HA epitope 306–324 [HA 306–324] of the sequence:
Cys-Pro-Lys-Tyr-Val-Lys-Gln-Asn-Thr-Leu-Lys-Leu-Ala-Thr-Gly-Met-Arg-Asn-Val The cytotoxic T-lymphocyte (CTL) epitopes used in the vaccine of the invention will change according to the population type, namely Caucasian or non-Caucasian (of Asian or African origin). For Caucasian populations, the preferred CTL epitopes are the influenza virus nucleoprotein (NP) epitope 335–350 [NP 335–350] of the sequence:

Ser-Ala-Ala-Phe-Glu-Asp-Leu-Arg-Val-Leu-Ser-Phe-Ile-Arg-Gly-Tyr and the NP epitope 380–393 [NP 380–393] of the sequence:

Glu-Leu-Arg-Ser-Arg-Tyr-Trp-Ala-Ile-Arg-Thr-Arg-Ser-Gly

In a preferred embodiment of the invention, the intranasal influenza vaccine consists of a mixture of the four influenza virus epitopes: hemagglutinin epitopes HA91–108 and HA307–319, and nucleoprotein epitopes NP335–350 and NP380–393, expressed individually in Salmonella flagellin. For non-Caucasian populations, other CTL epitopes can be used.

The present invention also relates to the use of a mixture of flagella containing at least four epitopes of influenza virus each expressed individually in Salmonella flagellin, as described above, for the preparation of a human synthetic influenza vaccine for intranasal administration.

The present invention further relates to a method for inducing a human immune response and conferring protection against influenza virus in humans, which comprises administering intranasally to human individuals a synthetic peptide-based influenza vaccine comprising a mixture of flagella, as described above.

BRIEF DESCRIPTION OF THE DRAWINGS

In the following legends, "tetra construct" means a mixture of the flagella expressing the four influenza epitopes HA91–108, HA307–319, NP335–350 and NP380–393, respectively.

FIGS. 1A–1B depict typical FACS histograms of human lung lymphocytes in human/mouse radiation chimera, immunized with the tetra construct. The samples were taken 7 days after the immunization. The cells were separated on phicoll gradient and stained with anti-CD45 together with anti-CD3 (FIG. 1A) or together with anti-CD19 (FIG. 1B), conjugated to the respective fluorescence dye. The histograms show that after immunization most of the human cells are T cells and almost no B cells can be detected.

FIG. 2: Lungs homogenates from the immunized and non-immunized mice as well as a group of non-transplanted mice were analyzed for the virus titer 5 days after viral challenge. The mice were immunized with the tetra construct (left block) or native flagellin that does not express the influenza epitopes (middle block). Another control group did not receive PBMC but were immunized with the tetra construct (right block). The figure presents mean data from 7 repeated experiments, in which each group consisted of 6–8 animals. In each experiment different donor was employed.

FIG. 3: Human antibodies production (total amount of IgG, IgM and IgA), in human/mouse radiation chimera (6–8 animals per group in 7 repeated experiments, different donor employed in each experiment) immunized with the tetra construct (left column) or native flagellin that does not express the influenza epitopes (middle column). Another control group did not receive PBMC, but was immunized with the tetra construct (right column). Sera samples were diluted 1:10, lungs samples were diluted 1:60. Ab production in the group that was transplanted and vaccinated with the tetra construct (left column) was significantly higher than in the other control groups.

FIG. 4: Percent survival of human/mouse radiation chimera from lethal challenge after intranasal vaccination with the tetra construct. The mice (5–10 animals per group in 2 repeated experiments, different donor employed in each experiment) were transplanted with PBMC on day 0, vaccinated on day 9 and challenged 7 days later. Vaccination with the tetra construct (black circles), native flagellin (hollow circles) or non-transplanted mice that were vaccinated with the tetra construct: (squares). After day 40, the survival rate remained the same and all the surviving mice eventually recovered.

FIG. 5: Body weight of surviving mice, which is indicative of disease severity and the potential for a recovery process. Human/mouse radiation chimera (5–10 animals per group in 2 repeated experiments, different donor employed in each experiment) were transplanted with PBMC on day 0, vaccinated intranasally on day 9 and challenged intranasally 7 days later with a lethal dose of the virus. Mice vaccinated with the tetra construct (black circles) lost less weight and recovered more quickly than the other groups. Control groups consisted of transplanted mice that were administered with native flagellin (hollow circles) or non-transplanted mice that were vaccinated with the tetra construct (squares). After day 40, all the surviving mice slowly recovered and gained weight.

FIG. 6: Protective vaccination of human/mouse radiation chimera transplanted with PBMC and immunized intranasally with the tetra construct. Each group of human/mouse chimera (5–10 animals per group in 2 repeated experiments, different donor employed in each experiment) transplanted with PBMC obtained by leukapheresis from one donor was infected 7 days after the immunization with one of three different influenza strains: A/PR/8/34 (H1N1), A/Japanese/57 (H2N2) or A/Texas/1/77 (H3N2). Both transplanted (left column) and non-transplanted (right column) mice were vaccinated with the tetra construct. However, only the transplanted mice were able to resist the infection and the virus titer in their lungs is significantly reduced.

FIG. 7: Serum human antibodies towards influenza virus following immunization of lethally irradiated human/mouse radiation chimera (5–10 per group) radioprotected with $3\times10^6$ SCID bone marrow (BM) and transplanted with $70\times10^6$ human PBMC. All the groups were immunized with the tetra construct and then challenged with sub-lethal dose of H1N1 strain (black lozenges) or H2N2 (black circles) or H3N2 (black squares). The control group consisted of irradiated SCID replenished mice that did not receive PBMC and were immunized with the same vaccine prior to challenge with H1N1 (hollow lozenges) or H2N2 (hollow circles) or H3N2 (hollow squares).

DETAILED DESCRIPTION OF THE INVENTION

The concept of peptide-based vaccine holds several advantages over traditional vaccines, including safety considerations, the relatively long shelf-life, the ability to target the immune response towards specific epitopes that are not suppressive nor hazardous for the host and the possibility of preparing multi-pathogen vaccine. The efficacy of a peptide vaccine is highly dependent on the exact identification of the immunogenic epitopes that confer protection as well as the efficient presentation of these epitopes to the immune system.

The idea of a peptide vaccine for influenza which includes both B and T cells epitopes was previously tested in a mouse model, and it has been shown that such a "vaccine" could induce specific local response in the lungs that led to protection of the immunized mice from viral challenge (Arnon and Levi, 1996). In the mice model used there, it was shown that the B cell epitope indeed induced high Ab production, while the T helper epitope elicited specific lymphocyte proliferation and the CTL epitope was important for cytotoxic activity against infected cells. However, efficient protection was achieved only when the mice were immunized with a mixture of all three epitopes (Levi and Arnon, 1996).

According to the present invention, for the purpose of human use, appropriate epitopes had to be selected because the T-cell epitopes are MHC-restricted. First, we have identified that at least four influenza epitopes are necessary for human use: one B-cell HA epitope, one T-helper HA or NP epitope that can bind to many HLA molecules, and at least two CTL NP or matrix epitopes that are restricted to the most prevalent HLA molecules in the different populations.

According to the invention, a preferred B-cell influenza epitope is HA 91–108. Preferred T-helper influenza epitopes are HA 307–319 and HA 306–324 (Rothbard, 1988), but also NP 206–229 (Brett, 1991) may be used.

The CTL influenza epitopes are different in the Caucasian, the Asia- or the Africa-originated population. For the Caucasian population, the preferred influenza CTL epitopes are NP335–350 and NP380–393 (Dyer and Middleton, 1993; Gulukota and DeLisi, 1996), that are restricted to the most prevalent HLA molecules in the Caucasian population. Other influenza epitopes that can be used according to the invention for the Caucasian population are the nucleoprotein epitopes: NP305–313 (DiBrino, 1993); NP384–394 (Kvist, 1991); NP89–101 (Cerundolo, 1991); NP91–99 (Silver et al, 1993); NP380–388 (Suhrbier, 1993); NP44–52 and NP265–273 (DiBrino, 1994); and NP365–380 (Townsend, 1986); and the matrix protein (M) epitopes M2–22, M2–12, M3–11, M3–12, M41–51, M50–59, M51–59, M134–142, M145–155, M164–172, M164–173 (all described by Nijman, 1993); M17–31, M55–73, M57–68 (Carreno, 1992); M27–35, M232–240 (DiBrino, 1993).

For non-Caucasian populations, the influenza CTL epitopes that can be used are HA458–467 of the sequence Asn-Val-Lys-Asn-Leu-Tyr-Glu-Lys-Val-Lys (NVKNLYEKVK), a CTL epitope for allele All with high frequency in Japanese, Chinese, Thais and Indian populations (J. Immunol. 1997, 159(10): 4753–61); M59–68 and M60–68 of the sequences Ile-Leu-Gly-Phe-Val-Phe-Leu-Thr-Val (ILGFVFTLTV) and Leu-Gly-Phe-Val-Phe-Leu-Thr-Val (LGFVFTLTV), respectively, two CTL epitopes for HLA-B51 with high frequency in Thais population (Eur. J. Immunol. 1994, 24(3): 777–80); and M128–135 of the sequence Ala-Cys-Ser-Met-Gly-Leu-Ile-Tyr (ACSMGLIY), a CTL epitope for allele B35 with high frequency in negroid West African population (Eur. J. Immunol. 1996, 26(2): 335–39).

Since peptides are usually poor immunogens, the efficacy of peptide-based vaccine depends on the adequate presentation of the epitopes to the immune system. The influenza epitopes were expressed in the flagellin gene of Salmonella vaccine strain, which provides both carrier and adjuvant function. After cleavage of the flagella from the bacteria and the purification steps, the fine suspension of the flagella was used for vaccination. All immunizations were performed with a mixture of the four epitopes: HA91–108, HA307–319, NP335–350 and NP380–393, expressed in Salmonella flagellin, in the absence of any adjuvant. The mixture of said four epitopes is referred to as "tetra construct" throughout the specification.

The three T-cell epitopes used in the vaccine of the present invention were selected due to their specific recognition by the prevalent HLA's in the Caucasian population, and were included in the vaccine together with the HA 91–108 B cell epitope. In order to overcome the problem of antigenic variation of the virus, all these epitopes are derived from conserved regions in the virus proteins and hence, can induce cross-strain protection. The two CTL epitopes from the inner nucleoprotein are recognized by the prevalent HLAs of the Caucasian population: the NP 335–350 epitope is restricted to A2, A3, Aw68.1 and B37 HLA haplotypes, and the NP 380–393 epitope is restricted to B8 and B27 HLA haplotypes. The T- helper epitope from the hemagglutinin, HA 307–319, is a "universal" epitope restricted to most of MHC class II molecules, including DR1, DR2, DR4, DR5, DR7, DR9, DR52A, and others. These T-cell epitopes, together with the B-cell epitope HA 91–108, were expressed individually in flagellin and the mixture of resultant flagella was used without any adjuvant for intranasal vaccination of human/mouse radiation chimera, thus inducing a human immune response and conferring protection. The vaccinated mice were also protected from a lethal infection and their recovery was quicker.

To evaluate the capacity of such tetra construct to act as a vaccine and stimulate a response of the human immune system, a humanized mouse model was employed. The observation that human PBMC can be adoptively transferred i.p. into the SCID mouse and that the engrafted cells survive for an extended period of time producing high levels of human Ig, has offered many new possibilities in clinical immunology research (reviewed in Mosier, 1991). In particular, many researchers have been utilizing this model for studying the capacity of engrafted lymphocytes to generate primary and secondary human humoral responses, and for viral research studies.

Recently, Lubin et al, 1994, described a new approach enabling engraftment of human PBMC in normal strains of mice following split-dose lethal irradiation which allows an effective and rapid engraftment of human cells. As previously reported, in such human/mouse radiation chimera, a marked human humoral as well cellular (CTL) responses could be generated by immunization with either foreign antigens or with allogeneic cells (Marcus et al, 1995; Segal et al, 1996), rendering advantages to this model in comparison to the previously used Mosier's SCID mouse model. Further advantages of this model is that the dissemination of engrafted lymphocytes is very rapid and both B and T lymphocytes were found by FACS analysis in significant numbers in the lymphoid tissues within a few days post transplantation (Burakova et al, 1997).

For evaluating the efficacy of a human influenza vaccine according to the invention, we used this human/mouse radiation chimera model. Although the number of human B cells after transplantation was low (FIG. 1), the chimeric mice were able to produce specific antibodies in response to i.p. administration of antigens. This is in accord with previous findings, showing that towards the second week post-transplantation, the engrafted human B and T cells form follicles in the spleen and lymph nodes. Furthermore, their phenotype was that of memory cells, namely mostly CD45RO positive and CD45RA negative (Burakova et al, 1997).

According to the present invention, the human/mouse radiation chimera were immunized with the tetra construct administered by the intranasal route. This is the first report of induction of local immune response in the nasal cavity and lungs following intranasal immunization in the human/mouse radiation chimera.

The induction of local immune response in the lungs was demonstrated by the presence of specific anti-influenza antibodies in the lungs homogenates (FIG. 3), by elevation of CD8+ lymphocytes proportion and by the viral clearance as a result of immunization with the tetra construct (FIG. 2). The tetra flagellin construct could also protect the mice from a lethal dose challenge of the virus, which is the ultimate demonstration of the protective effect. Under these conditions, in which the challenge dose is orders of magnitude higher than that pertaining in natural infection, all the chimera were infected regardless of their immune state. However, whereas none of the immunized mice that had not been transplanted with the human lymphocytes survived the infection, and only 50% of the transplanted but not immunized mice survived, the transplanted and immunized group was completely protected and showed 100% survival (FIG. 4).

The partial protection in the non-vaccinated mice is probably due to polyclonal stimulation and expansion of memory cells originating from the donor. This could be due to either previous exposure of the donor to the antigen or because it is cross-reactive to some extent with other recall antigens, a phenomena that was previously reported for other antigens (Marcus et al, 1995).

Figure 4:
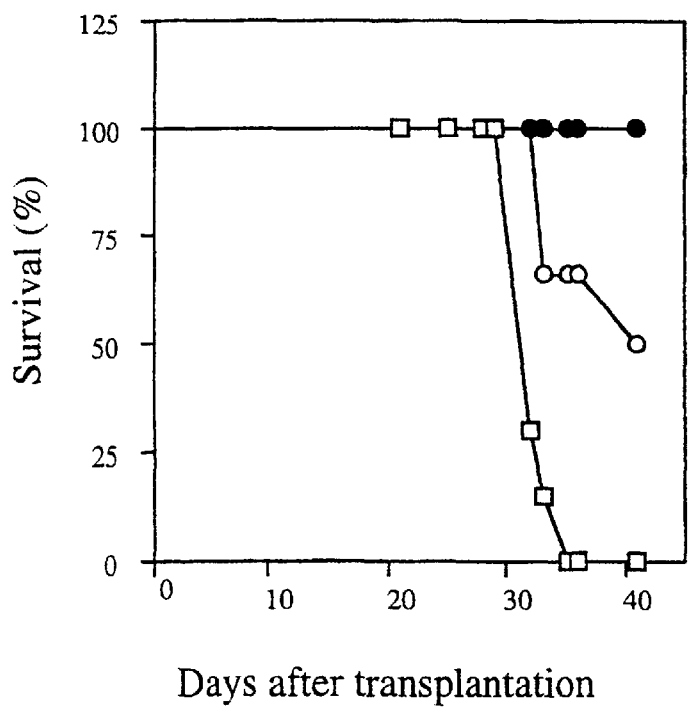
Figure 5:
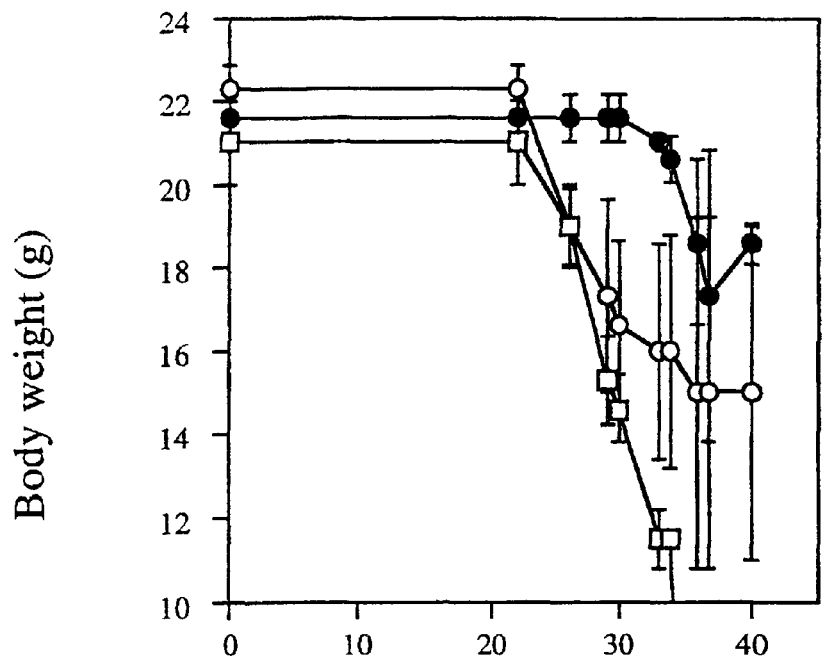

However, although such partial protection was indeed observed, a significant difference in the efficacy of the recovery process between the immunized and non-immunized groups was observed as evident both by survival rate and by their weight loss pattern (FIGS. 4, 5). Although the HLA phenotypes of the PMBC donors were not determined, all of the transplanted mice were protected as a result of the vaccination, indicating that the epitopes used in the present invention are indeed recognized by a wide range of HLA molecules.

Figure 6:
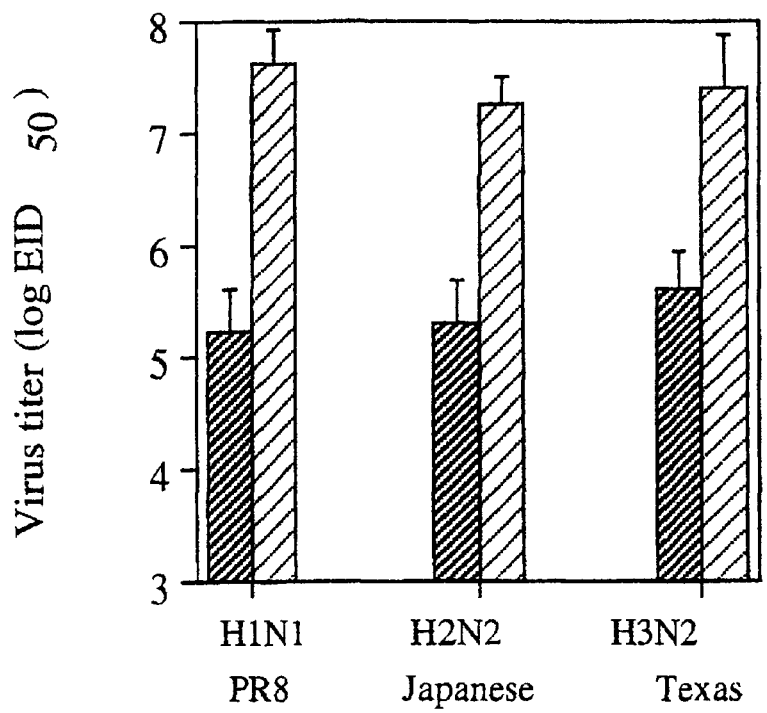

One of the most acute problems related to currently existing influenza vaccines is the narrow range of their specificity and their restricted strain-specific activity. The rapid variation in the viral surface glycoproteins leads to appearance of new strains with high variability in their serospecificity, and hence the vaccines containing the outer glycoproteins of some specific strains are limited in their efficacy to these strains. According to the present invention, we also established the cross-protection capacity of the tetra construct vaccine. All the epitopes that were included in the tetra construct are conserved regions in the respective proteins, and consequently, antibodies against the recombinant flagella could recognize various influenza strains (Table 1). Consequently, immunization of the chimeric mice with the epitopes led to production of specific antibodies and to their protection from sub-lethal dose infection by three different influenza strains, of the H1, H2 or H3 specificity (FIG. 6).

Thus, the results with the tetra construct according to the invention demonstrate the ability of a synthetic peptide-based vaccine to confer protection against influenza viral challenge. The recombinant flagellin construct indeed presents the influenza B and T-cell epitopes to the human immune cells in an efficient manner and induces both humoral and cellular responses. Since the employed T cell epitopes are recognized by a variety of HLA molecules, the vaccine was effective in all the experiments in which different donors with unknown HLA typing were utilized, indicating the applicability of this approach for a human vaccine in a heterologous population.

EXAMPLES

Materials and Methods 1 Mice. BALB/c mice (4–8 weeks old) were obtained from Olac Farms (Bicester, U.K.), NOD/SCID mice (4–6 weeks old) from the Weizmann Institute Animal Breeding Center (Rehovot, Israel). All mice were fed sterile food and acid water containing ciprofloxacin (20 $\mu$g/ml).

2 Conditioning regimen. BALB/c mice were exposed to a split lethal total body irradiation (TBI) of 4 Gy followed 3 days later by 10 Gy. The source of radiation is a gamma beam 150-A $^{60}$Co (produced by the Atomic Energy of Canada, Kanata, Ontario). Bone marrow cells from NOD/SCID mice (4–6 weeks old) were obtained according to Levite et al., 1991. Recipient irradiated mice were injected with 2–3×10$^6$ SCID bone marrow cells (i.v. in 0.2 ml phosphate-buffered saline (PBS)) one day after irradiation.

3 Preparation and transplantation of human peripheral blood lymphocytes. Buffy coats from normal volunteers were layered onto Lymphoprep solution (Nyc6med, Oslo, Norway) and spun at 2000 rpm for 20 min. The interlayer was collected, washed twice, counted and resuspended in PBS pH 7.4, to the desired cell concentration. Human PBMC (70×10$^6$ cells in 0.5 ml PBS) were injected i.p. into recipient mice, conditioned as described above. Control mice did not receive human PBMC.

4 Leukapheresis procedure. Leukapheresis was performed on normal volunteers. Cells were collected by processing 3–4 liters of blood through Haemonetics V50 (USA) during 3–3.5 hours. The Leukapheresis product was centrifuged at 1200 rpm for 10 min. and the plasma removed.

5 Chimeric flagellin. Oligonucleotides corresponding to the designated influenza epitopes, namely NP335–350 (SAAFEDLRVLSFIRGY), NP380–393 (ELRSRYWAIRTRSG) and two peptides from the H3 subtype haemagglutinin: HA91–108 (SKAFSNCYPYDVPDYASL) and HA307–319 (PKYVKQNTLKLAT) were synthesized in a 380B Applied Biosystems DNA Synthesizer, with additional GAT sequence at the 3' of each oligonucleotide in order to preserve the EcoRV restriction site, as described (Levi and Arnon, 1996). The synthetic oligonucleotides were inserted at the EcoRV site of the plasmid pLS408 and eventually transformed into a flagellin negative live vaccine strain (an Aro A mutant) of *Salmonella dublin* SL5928 by transduction, using the phage P22HT105/1 int. Finally, the flagella were purified after acidic cleavage and a fine suspension was used for immunization (Levi and Arnon, 1996).

6 Preparation of recombinant bacteria. The construction of the expression vector pLS408 is described by Newton et al., 1989, herein incorporated entirely by reference. The synthesized oligonucleotides were inserted at the EcoRV site of the plasmid pLS408, and transformed into *E. coli* JM101 competent cells. Colonies containing the recombinant plasmid were selected by probing them with one of the oligonucleotides labeled with $^{32}$p-ATP. Plasmids from positive colonies were purified and the insert orientation was determined using restriction analysis. The desired plasmids were used to transform *Salmonella typhimurium* LB5000 (a restrictive negative, modification proficient non flagellated) competent cells (Bullas and Ryu, 1983, herein entirely incorporated by reference) and were then transferred to a flagellin negative live vaccine strain (an Aro A mutant) of *Salmonella dublin* SL5928 by transduction using the phage P22HT105/1 int (Orbach and Jackson, 1982, and Schmieger, 1972, both herein entirely incorporated by reference). The transformed *S. dublin* were selected for ampicillin resistance, motility under the light microscope and growth in semisolid LB agar plates, supplemented with Oxoid nutrient broth #2. Selected clones were grown overnight in 2 liters of LB amp. Medium and the flagellin was purified by acidic cleavage, according to the technique described by Ibrahim et al., 1985, herein entirely incorporated by reference.

7 Isolation of flagella. Flagella were isolated according to Ibrahim et al., 1985: Bacterial cells from an overnight culture grown in LB/ampicillin medium were pelleted and suspended in a small volume of PBS. The pH was reduced with 1 M HCl to 2.0 and the suspension was incubated at room temperature for 30 minutes with gentle agitation. The stripped cells were removed by centrifugation at 5000 rpm for 15 minutes and the pH was readjusted to 7.4. The flagella were then precipitated by $(NH_4)_2SO_4$ (35% w/v) and maintained overnight at 4° C. The pellet obtained after centrifugation at 10,000 rpm for 10 minutes at 4° C. was dissolved in PBS, dialyzed against a large volume of PBS at 4° C. and any formed precipitate was discarded. The resultant protein was stored at −20° C. This resulting flagella is an aggregate of the flagellin protein and may be used as such for a vaccine. Presence of the chimeric flagellin HA and NP epitope protein of the invention are shown in FIG. 2 after SDS-PAGE of the flagella.

8 Immunization and infection of chimeric animals. On the ninth day after PBMC transplantation, human/mouse chimera were immunized once, intranasally with a mixture of 25 µg of each hybrid flagellin construct in total volume of 50 µl PBS or, in the control group, with 75 µg of the native flagella. This amount was predetermined as the optimal dose in a preliminary experiment in BALB/c mice. Infection of mice was performed 7 days later by inoculating intranasally the infectious allantoic fluid, 50 μl $10^{-4}$ HAU virus per mouse, In both immunization and infection, the mice were under a light ether anesthesia. The chimera were sacrificed on the 5th day after infection. Their lungs were removed for viral titration.

9 FACS analysis of donors PBMC and human cell engraftment in chimeric mice. For the evaluation of human cell engraftment in the human/mouse chimera, mice engrafted with human lymphocytes were sacrificed 27–29 days after PBMC transplantation. Lymphocytes from lung homogenates as well as peritoneal washes were separated on ficoll-paque gradient (Pharmacia Biotech AB, Upsala, Sweden) and then incubated for 30 min on ice with a mixture of appropriate fluorescently-labeled monoclonal antibodies. After washing, double fluorescent analysis of human antigens was performed on a FACScan analyzer (Beckton-Dickinson, CA). The following antibodies that recognize specific human surface molecules were used: anti-CD45-phycoerythrine (PE)(clone HI30) from Pharmigen; anti-CD3-peridinin chlorophyll protein (PerCP) (clone SK7); and anti-CD19-FITC (clone 4G7) (Beckton-Dickinson, CA).

10 Human immunoglobulin determination. Total human Ig was quantified in sera samples by sandwich ELISA using goat F(ab)2 —purified anti-human Ig (G+M+A) (Sigma) as the capture agent and peroxidase-conjugated purified goat anti-human Ig (G+M+A) (Sigma) as the detection reagent. Human serum of known immunoglobulin concentration was used as the standard. ELISA was performed as described by Marcus et al., 1995.

11 Determination of human immunoglobulins specific for influenza. Lung homogenates and sera were tested for specific anti-influenza human antibodies, The virus (100 HAU/ml) was adsorbed to ELISA plates and blocking was performed with 1% bovine serum albumin (BSA) in PBS. Rabbit anti-human Ig, conjugated to horseradish peroxidase (Sigma) were used as second antibodies. Following the addition of the substrate (ABTS) the plates were read at 414 nm.

12 Influenza virus. The influenza strains A/PR/8/34 (H1N1), A/Japanese/57 (H2N2) and A/Texas/1/77 (H3N2) were used. Virus amounts were measured in hemagglutination units (HAU). For immunization, the inactive virus (A/Texas/1/77), purified by sucrose gradient was used. Virus growth and purification were according to standard methods (Barret and Inglis, 1985). For virus titration, lung samples were homogenized in PBS containing 0.1% BSA and centrifuged in order to remove debris. Virus titers were determined by whole egg titration method (Barret and Inglis, 1985). The titer was calculated by hemagglutination and presented as Log $EID_{50}$ (Thompson, 1947).

13 Statistical analysis. Statistical analysis was performed using the Stat View II program (Abacus Concepts Inc., Berkeley, Calif., USA) on a Macintosh IICi. F-test was utilized to calculate probability (p) values. Results are presented as mean and standard error of at least two repeated independent experiments, including 5–10 animals per group.

EXAMPLE 1

Response of the Chimeric Mice to Whole Inactivated Influenza Virus

In order to establish the suitability of the human/mouse radiation chimera for evaluating the synthetic peptide-based vaccine, we have first evaluated their immune response towards inactive purified influenza virus which is known to be protective. The mice were immunized i.p. with 50 μg of the virus on the day of PBMC transplantation, followed by a sublethal viral challenge with influenza A/Texas/1/77 strain 14 days after immunization. The vaccination of human/mouse radiation chimera with the whole killed virus vaccine, without any adjuvant, induced production of specific antibodies—the serum antibody titer was significantly higher (2.4 fold) in the immunized chimera as compared to the control group. Moreover, this vaccination markedly reduced the subsequent virus infection. The lung virus titer after challenge was significantly lower (by 2.7 orders of magnitude) in the immunized chimera as compared to the control group.

After thus demonstrating the suitability of the human/mouse radiation chimera for evaluating the anti-influenza response following the immunization with inactive influenza virus, we proceeded with the evaluation of the synthetic peptide-based recombinant vaccine designed for humans in this humanized mouse model.

EXAMPLE 2

FACS Analysis of Immunized Mice for Evaluating the Engraftment of Human PBMC in Human/BALB Chimera The successful engraftment of the human cells in the human/mouse chimera was demonstrated in a preliminary experiment showing that most of the lymphocytes in the peritoneum (50–80%) and in the lungs of the mice (30–60%) were of human origin. For the evaluation of human cell engraftment in the human/mouse chimera, the presence of human cells in the engrafted mice was analyzed by FACS.

FIG. 1 is a FACS histogram depicting the pattern of human lung lymphocytes after immunization with the tetra construct without further challenge infection. The cells were stained with anti-CD45 antibodies together with anti-CD3 or together with anti-CD19. As shown, most of the human cells (stained with anti-CD45) are CD3+, namely T cells (80%–90%) and only a minor population is CD19+

(3%–10%). Similar data were obtained for human lymphocytes in the peritoneum. It is of interest that the CD8+/CD4+ ratio in the immunized mice ranged between 1 and 2 as compared to a ratio of 0.3–0.5 in the untreated chimera. This disproportionate expression of CD8 cells may suggest that they play a role in the observed protection.

EXAMPLE 3

Virus Clearance From the Lungs Following Sub-lethal Challenge

Influenza infection is a respiratory disease, hence, a local immune response induced by an intranasal administration of the vaccine could be more efficient than parenteral administration. The immunization schedule was modified in order to adapt it for intranasal immunization.

The mice (6–8 per group in 7 repeated experiments) were immunized intranasally (i.n.) 10–12 days after PBMC transplantation, as described in the Methods. Ten days later, they were challenged i.n. with $10^{-4}$ HAU in 50 $\mu$l allantoic fluid of live A/Texas/1/77 strain of influenza virus. Five days later they were sacrificed and their lungs were removed for virus titration. As shown in FIG. 2, which depicts the cumulative results, the vaccination with the tetra construct enabled the chimera to clear the virus from their lungs significantly more efficiently than the group vaccinated with the native flagella, or the group which was not transplanted with PMBC but were immunized with the tetra construct. Although the same percentage of human T lymphocytes was detected in both transplanted groups (FIG. 1), only the mice vaccinated with the hybrid flagellin show the ability to reduce virus burden, indicating specific and efficient local response in the lungs.

Human antibodies production in these mice was evaluated both in the serum (before challenge) and in the lungs (after challenge). Immunization with the tetra construct resulted in significantly higher titer of human antibodies specific for the virus in both serum and lungs samples (FIG. 3). It thus seems that although the proportion of CD19+ lymphocytes as detected by FACS analysis was similarly low in the immunized and control transplanted mice, the production of specific anti-influenza antibody response differs significantly between the two groups.

EXAMPLE 4

Survival and weight Loss Pattern After Lethal Dose of Viral Infection

Further to the sub-lethal infection challenge experiment, the ability of the tetra construct preparation to protect human/mouse chimera from a lethal dose of influenza virus was examined. FIG. 4 describes the results of two repeated experiments and demonstrates the survival of vaccinated and non-vaccinated mice (both transplanted with human PBMC), as well as of another control group that was not transplanted but was vaccinated with the tetra construct. As can be seen, while all control mice that were immunized with the tetra construct but had not been transplanted with the human lymphocytes died within 19 days after the infection, 100% survival was observed in the mice that received the PBMC prior to immunization. This indicates that survival is due to the response of the transplanted human immunocompetent cells. The PBMC by themselves provided a limited beneficial effect, as 50% survival was observed in the control group that was vaccinated with the native flagellin, that itself does not induce any anti-influenza protective response.

In FIG. 5, the body weight loss pattern of the challenged mice is depicted: the transplanted group that was immunized with the tetra flagellin construct, shows only a slight reduction in their body weight following the lethal dose infection and a rapid return to normal, while the control group that was transplanted with human PMBC but immunized with the native flagellin, lost more weight (the body weight is significantly different between the experimental group and the control groups on days 22–33 after transplantation) and the surviving mice started to recover weight only on the last days of the experiment. The non-transplanted, vaccinated control group lost weight rapidly and did not recuperate. The survival of the transplanted group that was immunized with the native flagella is better than that of the non-transplanted group probably due to some memory anti-influenza response of the donor's cells.

EXAMPLE 5

Protection From Infection With Different Strains of Influenza

Figure 7:
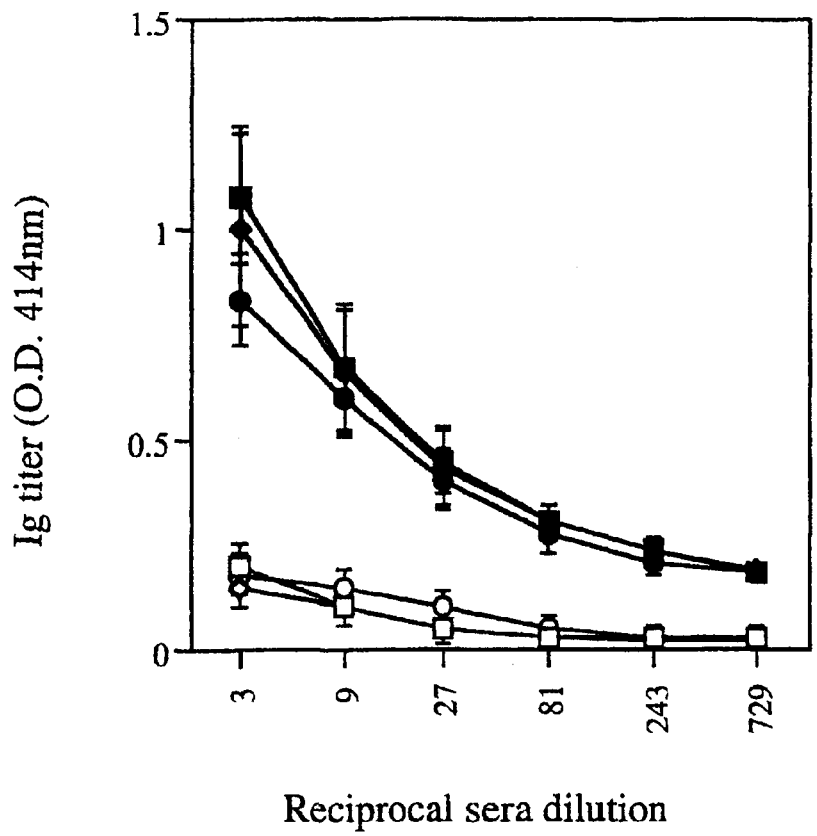

One of the major problems with currently available influenza vaccines is that they are effective only against the strains included in the vaccine. Therefore, it was of interest to examine the ability of the flagellin hybrids that express influenza epitopes to protect mice from different influenza strains that carry various hemagglutinin and neuraminidase glycoproteins. The B-cell epitope that is expressed in the flagellin is conserved in all influenza H3 subtypes, while the T-cell epitopes are from regions of the hemagglutinin and nucleoprotein highly conserved in other subtypes as well. In the first step, it was shown that rabbit antibodies towards these epitopes can indeed recognize and react in ELISA with different strains of influenza including A/Texas/1/77, A/Aichi/68, A/PR/8/34 and A/Japanese/57 (Table 1). To further test the potential of these epitopes to confer cross protection in humans, the human/mouse radiation chimera (8 mice per group) were immunized i.n. with the tetra construct. Their resistance to different influenza strains challenge was detected 7 days later and compared to non-transplanted mice that were immunized with the same flagella mixture. The influenza strains that were used for infection were: A/Texas/1/77 (H3N2), A/Japanese/57 (H2N2) and A/PR/8/34 (H1N1). Protective immunity was observed against all three strains, as presented in FIG. 6. Human Ig specific for each influenza strain was detected in the sera of all the transplanted and vaccinated mice, but not in the control group, as shown in FIG. 7.

TABLE 1

| Influenza virus strain | Ab Anti NP 335–350 | Ab anti NP 380–393 | Ab anti HA 91–108 | Ab anti HA 307–319 | Ab anti Virus (Texas) |
|---|---|---|---|---|---|
| A/Texas/1/77 | ++ | + | +++ | +− | +++ |
| A/Aichi/68 | +++ | ++ | +++ | ++ | +++ |
| A/P.C./73 | +++ | + | ++ | +− | +++ |
| A/England/42/72 | +++ | + | +++ | + | +++ |
| A/PR/8/34 | +++ | ++ | +++ | ++ | +++ |
| A/Japanese/57 | +++ | +− | +++ | +− | +++ |
| A/X/31 | +++ | + | +++ | +++ | +++ |
| B/Victoria/2/87 | +++ | + | ++ | +++ | +++ |

Rabbits immunized with four influenza epitopes (NP 335–350, NP 380–393, HA 91–108 and HA 307–319) conjugated to BSA, produced antibodies the specificity of which was determined by ELISA. These antibodies recognized different strains of influenza virus that were coating the ELISA microplates. The recognition between antibodies raised against the whole virus (A/Texas/1/77) serves as a positive control. Sera samples were tested in 1:150 dilution, and the antibodies recognition was scaled according to the maximal O.D.: +++=O.D>2; ++=O.D 1-2; +O.D 0.5-1; +−=O.D<0.5;

References

1. Arnon, R. and Levi, R. Synthetic recombinant vaccine induces anti-influenza long-term immunity and cross strain protection, In: *Novel Strategies in Design and Production of Vaccines* (Ed.: Cohen, S. and Shafferman, A.) Plenum Press, N.Y., 1996, p. 23.
2. Barrett, T. and Inglis, S. C. Growth purification and titration influenza viruses, In: *Virology: A practical approach* (Ed. Mahy, W. J.) IRL Press, Wash. D.C., 1985, pp. 119–151
3. Brett et al. *J. Immunol.* 1991. 147:984–991.
4. Bullas, L. R. and Ryu, J. *J. of Bacteriol.* 1983. 156:471–74.
5. Burakova, T., Marcus, H., Canaan, A., Dekel, B., Shezen, E., David, M., Lubin, I., Segal, H. and Reisner, Y. Engrafted human T and B lymphocytes form mixed follicles in lymphoid organs of human/mouse and human/rat radiation chimera. *Transplantation* 1997. 63:1166–1171
6. Carreno, B. M., Koenig, S., Coligan, J. E. and Biddison, W. E. The peptide binding specificity of HLA class I molecules is largely allele- specific and non-overlapping.*Mol Immunol* 1992. 29:1131–1140
7. Cerundolo et al. *Proc. R. Soc. Lon.* 1991. 244:169–7
8. DiBrino et al. *PNAS* 90. 1993. (4):1508–12
9. Dyer, P. and Middleton, D. In: *Histocompatibility testing, a practical approach* (Ed.: Rickwood, D. and Hames, B. D.) IRL Press, Oxford, 1993, p. 292.
10. Gulukota, K. and DeLisi, C. HLA allele selection for designing peptide vaccines. *Genetic Analysis: Biomolecular Engineering* 1996. 13:81.
11. Ibrahim, G. F. et al. *J. Clin. Microbiol.* 1985. 22:1040–1044
12. Kvist et al. Nature. 1991. 348:446–448
13. Laver, W. G., Air, G. M., Dopheide, T. A. and Ward, C. W. Amino acids sequence changes in the Hemagglutinin of A/Hong kong (H3N2) influenza virus during the period 1968–77. *Nature* 1980. 283:454–457
14. Laver, W., Air, G., Webster, R., Gerhard, W., Ward, C. and Dopheid, T. Antigenic drift in type A influenza virus: sequence differences in the Hemagglutinin of Hong-Kong (H3N2) variants selected with monoclonal hybridoma antibody.*Virology* 1980a. 98:226–237
15. Levi, R. and Arnon, R. Synthetic recombinant influenza vaccine induces efficient long-term immunity and cross-strain protection.*Vaccine* 1996. 14:85–92
16. Levite, M., Meshorer, A. and Reisner, Y. A rapid method for obtaining murine bone marrow cells in high yield. *Bone Marrow Transpl.* 1991. 8:1–3
17. Lubin, I., Segall, H., Marcus, H., David, M., Kulova, L., Steinitz, M., Erlich, P., Gan, J. and Reisner, Y. Engraftment of human peripheral blood lymphocytes in normal strains of mice.*Blood* 1994. 83:2368–2381
18. Marcus, H., David, M., Cnaan, A., Kulova, L., Lubin, I., Segal, H., Denis, L., Erlich, P., Galun, E., Gan, J., Laster, M. and Reisner, Y. Human/mouse radiation chimera are capable of mounting a human primary humoral response.*Blood* 1995. 86:398–406
19. Mosier, D. E. Adoptive transfer of human lymphoid cells to severely immunodeficient mice: models for normal human immune function, autoimmunity, lymphomagenesis, and AIDS. *Adv. Immunol.* 1991. 50:303–325
20. Newton, S. M. C. et al. *Science.* 1989. 244:70–72
21. Nijman et al. *Eur. J. Immunol.* 1993. 23:1215–1219
22. Orbach, M. J. and Jackson, E. N. *J. Bacteriol.* 1982. 149: 985–994
23. Rothbard, J. B., et al. *Cell.* 1988. 52(4):515–523
24. Schmieger, H. *Mol. Gen. Genet.* 1972. 119: 75–88
25. Segal, H., Lubin, I., Marcus, H., Canaan, A. and Reisner, Y. Generation of primary antigen-specific human cytotoxic T lymphocytes in human/mouse radiation cimera.*Blood* 1996. 88:721–730
26. Silver et al. *Nature.* 1993. 360: 367–369
27. Suhrbier, A., Schmidt, C. and Fernan, A. Prediction of an HLA B8-restricted influenza epitope by motif. *J. Immunology* 1993. 79:171–173
28. Thompson, W. R. Use of moving averages and interpolation to estimate median-effective dose.*Bacteriol. Rev.* 1947. 11:115–145
29. Townsend, A. R. M. and Skehel, J. J. *J. Exp. Med.* 1984. 160:552–563
30. Townsend, A. R. M. et al. *Cell.* 1985. 42:457–467
31. Townsend, A. R. M. et al. *Cell.* 1986. 44:959–968
32. Webster, R. G., Laver, W. G., Air, G. M. and Schild, G. C. Molecular mechanism of variation in influenza viruses.*Nature* 1982. 296:115–121

In the claims:

1. A human synthetic peptide-based influenza vaccine, comprising: at least four epitopes of influenza virus, said influenza virus epitopes being reactive with human cells, said epitopes comprising:
   (a) at least one B-cell hemagglutinin (HA) epitope comprising the influenza virus hemagglutinin epitope 91–108 according to SEQ ID NO:1;
   (b) at least one T-helper hemagglutanin (HA) epitope comprising the influenza virus hemagglutinin epitope 307–319 according to SEQ ID NO: 2 that can bind to many HLA molecules; and
   (c) at least two cytotoxic lymphocyte (CTL) nucleoprotein (NP) epitopes comprising the influenza virus nucleoprotein (NP) NP335–350 epitope according to SEQ ID NO:4 and the NP380–393 epitope according to SEQ ID NO:5 that are the most prevalent HLA molecules in a Caucasian human population, such that maximum stimulation of an immune system of a human subject occurs through a combination of at least two epitopes not being selective for a human population, and at least two epitopes being selective for a human population.

2. The vaccine of claim 1 wherein each of said epitopes is individually contained within a *Salmonella flagellin*.

3. The vaccine of claim 2 wherein a mixture of said flagellin comprises a tetra construct.

4. The vaccine of claim 1, being adapted for intranasal administration.

5. The vaccine of claim 1, further comprising an appropriate adjuvant.

6. The vaccine of claim 5, wherein said adjuvant comprises *Salmonella flagellin* for individual expression of each epitope, such that each epitope is contained within a flagella.

* * * * *

SEQUENCE LISTING

<160> NUMBER OF SEQ ID NOS: 9

<210> SEQ ID NO 1
<211> LENGTH: 18
<212> TYPE: PRT
<213> ORGANISM: Influenza virus

<400> SEQUENCE: 1

Ser Lys Ala Phe Ser Asn Cys Tyr Pro Tyr Asp Val Pro Asp Tyr Ala
 1               5                  10                  15

Ser Leu

<210> SEQ ID NO 2

-continued

```
<211> LENGTH: 13
<212> TYPE: PRT
<213> ORGANISM: Influenza virus

<400> SEQUENCE: 2

Pro Lys Tyr Val Lys Gln Asn Thr Leu Lys Leu Ala Thr
 1               5                  10

<210> SEQ ID NO 3
<211> LENGTH: 19
<212> TYPE: PRT
<213> ORGANISM: Influenza virus

<400> SEQUENCE: 3

Cys Pro Lys Tyr Val Lys Gln Asn Thr Leu Lys Leu Ala Thr Gly Met
 1               5                  10                  15

Arg Asn Val

<210> SEQ ID NO 4
<211> LENGTH: 16
<212> TYPE: PRT
<213> ORGANISM: Influenza virus

<400> SEQUENCE: 4

Ser Ala Ala Phe Glu Asp Leu Arg Val Leu Ser Phe Ile Arg Gly Tyr
 1               5                  10                  15

<210> SEQ ID NO 5
<211> LENGTH: 14
<212> TYPE: PRT
<213> ORGANISM: Influenza virus

<400> SEQUENCE: 5

Glu Leu Arg Ser Arg Tyr Trp Ala Ile Arg Thr Arg Ser Gly
 1               5                  10

<210> SEQ ID NO 6
<211> LENGTH: 10
<212> TYPE: PRT
<213> ORGANISM: Influenza virus

<400> SEQUENCE: 6

Asn Val Lys Asn Leu Tyr Glu Lys Val Lys
 1               5                  10

<210> SEQ ID NO 7
<211> LENGTH: 9
<212> TYPE: PRT
<213> ORGANISM: Influenza virus

<400> SEQUENCE: 7

Ile Leu Gly Phe Val Phe Leu Thr Val
 1               5

<210> SEQ ID NO 8
<211> LENGTH: 9
<212> TYPE: PRT
<213> ORGANISM: Influenza virus

<400> SEQUENCE: 8

Ile Leu Gly Phe Val Phe Leu Thr Val
 1               5

<210> SEQ ID NO 9
```

```
<211> LENGTH: 8
<212> TYPE: PRT
<213> ORGANISM: Influenza virus

<400> SEQUENCE: 9

Ala Cys Ser Met Gly Leu Ile Tyr
 1               5
```